(12) United States Patent
Crabtree

(10) Patent No.: US 7,214,228 B2
(45) Date of Patent: May 8, 2007

(54) TUNNEL PORT APPARATUS

(76) Inventor: John H. Crabtree, 4176 Rainwood Ave., Yorba Linda, CA (US) 92888-3136

( * ) Notice: Subject to any disclaimer, the term of this patent is extended or adjusted under 35 U.S.C. 154(b) by 770 days.

(21) Appl. No.: 10/342,728

(22) Filed: Jan. 14, 2003

(65) Prior Publication Data

US 2004/0138675 A1 Jul. 15, 2004

(51) Int. Cl.
*A61F 11/00* (2006.01)
*A61B 17/34* (2006.01)

(52) U.S. Cl. ..................... 606/108; 604/506

(58) Field of Classification Search ............... 606/108, 606/185; 604/506–507
See application file for complete search history.

(56) References Cited

U.S. PATENT DOCUMENTS

| | | | |
|---|---|---|---|
| 1,527,291 A | 2/1925 | Zorraquin | |
| 2,623,521 A | 12/1952 | Shaw et al. | 128/221 |
| 3,713,447 A | 1/1973 | Adair | 128/347 |
| 3,774,604 A | 11/1973 | Danielsson | 128/214.4 |
| 4,020,835 A | 5/1977 | Nordstrom et al. | 128/214.4 |
| 4,108,175 A | 8/1978 | Orton | 128/214 |
| 4,332,242 A | 6/1982 | Chikama | 128/3 |
| 4,351,333 A * | 9/1982 | Lazarus et al. | 604/28 |
| 4,403,617 A | 9/1983 | Tretinyak | 128/754 |
| 4,411,655 A | 10/1983 | Schreck | 604/165 |
| 4,417,886 A | 11/1983 | Frankhouser et al. | 604/53 |
| 4,535,773 A | 8/1985 | Yoon | 604/51 |
| 4,636,199 A | 1/1987 | Victor | 604/164 |
| 4,712,536 A | 12/1987 | Hawks | 128/3 |
| 4,772,266 A | 9/1988 | Groshong | 604/164 |
| 4,808,168 A | 2/1989 | Warring | 604/158 |
| 4,888,000 A | 12/1989 | McQuilkin et al. | 604/164 |
| 4,899,729 A | 2/1990 | Gill et al. | 128/3 |
| 4,972,827 A | 11/1990 | Kishi et al. | 128/3 |
| 5,125,903 A | 6/1992 | McLaughlin et al. | 604/167 |
| 5,141,498 A | 8/1992 | Christian | 604/167 |
| 5,183,464 A | 2/1993 | Dubrul et al. | 128/3 |
| 5,281,237 A | 1/1994 | Gimpelson | 606/144 |
| 5,334,159 A | 8/1994 | Turkel | 604/158 |
| 5,657,963 A | 8/1997 | Hinchliffe et al. | 251/149.1 |
| 5,727,770 A | 3/1998 | Dennis | 604/256 |
| 5,895,377 A | 4/1999 | Smith et al. | 604/256 |
| RE36,702 E | 5/2000 | Green et al. | 606/167 |
| 6,156,006 A | 12/2000 | Brosens et al. | 604/104 |

(Continued)

OTHER PUBLICATIONS

Crabtree et al; "A Laparoscopic Approach Under Local Anesthesia for Peritoneal Dialysis Access;" Peritoneal Dialysis International; vol. 20, No. 6; Nov. 2000.

(Continued)

*Primary Examiner*—Vy Bui
(74) *Attorney, Agent, or Firm*—Greenberg Traurig LLP; Robert Joseph Foster, Esq

(57) ABSTRACT

Provided herein is a port apparatus and method for inserting a tube device, in particular peritoneal dialysis catheters, into an organism. Access to the peritoneal cavity for dialysis is established by creating a controlled cutaneoperitoneal fistula with a catheter device that bridges the abdominal wall. The apparatus is designed to minimize the occurrence of mechanical complications associated with traditional catheter implantation techniques, such as catheter obstruction from the omentum, catheter displacement to a position of poor drainage function, leaks and hernias. The device is capable of performing its functions in a simple, safe, accurate, reproducible, and expeditious fashion.

13 Claims, 9 Drawing Sheets

U.S. PATENT DOCUMENTS

| | | | |
|---|---|---|---|
| 6,258,065 B1 | 7/2001 | Dennis et al. | 604/167.03 |
| 6,325,812 B1 | 12/2001 | Dubrul et al. | 606/185 |
| 6,439,541 B1 | 8/2002 | Nösel | 251/149.1 |
| 6,530,911 B1 * | 3/2003 | Utterberg | 604/506 |
| 6,589,212 B1 | 7/2003 | Navis | |
| 6,638,253 B2 | 10/2003 | Breznock | |

OTHER PUBLICATIONS

Zoran et al,; "Laparoscopic Placement of the Peritoneal Dialysis Catheter Using a Specially Designed Trocar: A Review of 84 Patients;" Dialysis & Transplantation; vol. 29, No. 11; Nov. 2000.
Adamson et al; "Endoscopic placement of CAPD catheters: a review of one hundred procedures;" Nephrol Dial Transplant; vol. 7; 1992; pp. 855-857.
Bhoyrul et al.; "Radially expanding dilatation: A superior method of laparoscopic trocar access;" Surg Endosc; vol. 10; 1996; pp.775-778.
Bierman et al.; "Peritoneal catheter survival and complications in end stage renal disease;" Perit Dial Bull; vol. 5; Oct.-Dec. 1985; pp. 229-233.
Bruns et al. "The cost of caring for end-stage kidney disease patients: an analysis based on hospital financial transaction records;" J Am Soc Nephrol; vol. 9, No. 5; May 1998; pp. 884-890.
Collins et al.; "Mortality risks of peritoneal dialysis and hemodialysis;" Am J Kidney Dis; vol. 34, No. 6; Dec. 1999; pp. 1065-1074.
Copley et al.; "Peritoneoscopic placement of swan neck peritoneal dialysis catheters;" Perit Dial Int; vol. 16, Supp. 1; Jun. 18-21, 1995; pp. S330-S332.
Cronen et al.; "Tenckhoff catheter placement: surgical aspects;" Am Surg; vol. 51; Nov. 1985; pp. 627-629.
Cruz et al.; "Peritoneoscopic implantation of catheters for peritoneal dialysis: effect on functional survival and incidence of tunnel infection;" Contrib Nephrol; vol. 89; 1991; pp. 35-39.
Draganic et al.; "Comparative experience of a simple technique for laparoscopic chronic ambulatory peritoneal dialysis catheter placement;" Aust NZ J Surg; vol. 68; 1998; pp. 735-739.
Eklund et al.; "Peritoneal dialysis access: a comparison of peritoneoscopic and surgical insertion techniques;" Scand J Urol Nephrol; vol. 32; 1998; pp. 405-408.
Favazza et al.; "Insertion of a straight peritoneal catheter in an arcuate subcutaneous tunnel by a tunneler: long-term experience;" Peritt Dial Int; vol. 15; 1995; pp. 357-362.
Fenton et al.; "Hemodialysis versus peritoneal dialysis: a comparison of adjusted mortality rates;" Am J Kidney Dis; vol. 30, No. 3; Sep. 1997; pp. 334-342.
Flanigan et al.; "The use and complications of three peritoneal dialysis catheter designs;" ASAIO Transactions; vol. 33; 1987; pp. 33-38.
Gadallah et al.; "Periitoneoscopic versus surgical placement of periitoneal dialysis catheters: a prospective randomized study on outcome;" Am J Kidney Dis; vol. 33, No. 1; Jan. 1999; pp. 118-122.
Gerhart; "Needleoscopic placement of Tenckhoff catheters;" J Soc Laparoendosc Surg; vol. 3 1999; pp. 155-1 58.
Gokal et al.; "What is the evidence that peritoneal dialysis is underutilized as an ESRD therapy?;" Semin Dial; vol. 15, No. 3; May-Jun. 2002; pp. 149-161.
Heaf et al.; "Initial survival advantage of peritoneal dialysis relative to haemodialysis;" Nephrom Dial Transplant; vol. 17; 2002; pp. 112-117.
Helfrich et al.; "Reduction of catheter complications with lateral placement;" Perit Dial Bull; vol. 3, No. 4; Oct.-Dec. 1983; pp. S2-S4.
Jacobs et al.; "Radiologic placement of peritoneal dialysis catheters: preliminary experience;" Radiology, vol. 182; 1992; pp. 251-255.
McMurray et al.; "Impact of capitation on free-standing dialysis facilities: Can you survive?;" Am J Kidney Dis; vol. 30, No. 4; Oct. 1997; pp. 542-548.
Mellotte et al.; "Peritoneal dialysis catheters: a comparison between percutaneous and conventional surgical placement techniques;" Nephrol Dial Transplant; vol. 8; 993; pp. 626-630.
Nahman et al.; "Modification of the percutaneous approach to peritoneal dialysis catheter placement under peritoneoscopic visualization: clinical results in 78 patients;" J Am Soc Nephrol; vol. 3, No. 1; 1992; pp. 103-107.
Nijhuis, et al.; "Laparoscopic introduction of a continuous ambulatory peritoneal dialysis (capd) catheter by a two-puncture technique;" Surg Endosc; vol. 10; 1996; pp. 676-679.
Öğünç; "Videolaparoscopy with omentopexy: a new technique to allow placement of a catheter for continous ambulatory peritoneal dialysis;" Surg Today; vol. 31; 2001; pp. 942-944.
Pastan et al.; "Prospective comparison of peritoneoscopic and surgical implantation of CAPD catheters;" ASAIO Transactions; 1991; pp. M154-M156.
Poole et al.; "Laparoscopic Tenckhoff catheter insertion: a prospective study of a new technique;" Aust NZ J Surg; vol. 70; 2000; pp. 371-373.
Spence et al.; "Improved results with a paramedian technique for the insertion of peritoneal dialysis catheters;" Surg Gyn Obstet; vol. 161; Dec. 1985; pp. 585-587.
Swartz et al.; "The curled catheter: dependable device for percutaneous peritoneal access;" Perit Dial Int; vol. 10; 1990; pp. 231-235.
Twardowski et al; "Long-term experience with swan neck Missouri catheters;" ASAIO Transactions; vol. 36; 1990; pp. M491 - M494.
Van Biesen et al.; "An evaluation of an integrative care approach for end-stage renal disease patients;" J Am Soc Nephrol; vol. 11, No. 1; Jan. 2000; pp. 116-125.
Xue et al.; "Forecast of the number of patients with endstage renal disease in the United States to the year 2010;" Clin Nephrol; vol. 12; 2001; pp. 2753-2758.
PCT/US03/40319 International Search Report, Jun. 25, 2004, by Officer Vy Q. Bui.

* cited by examiner

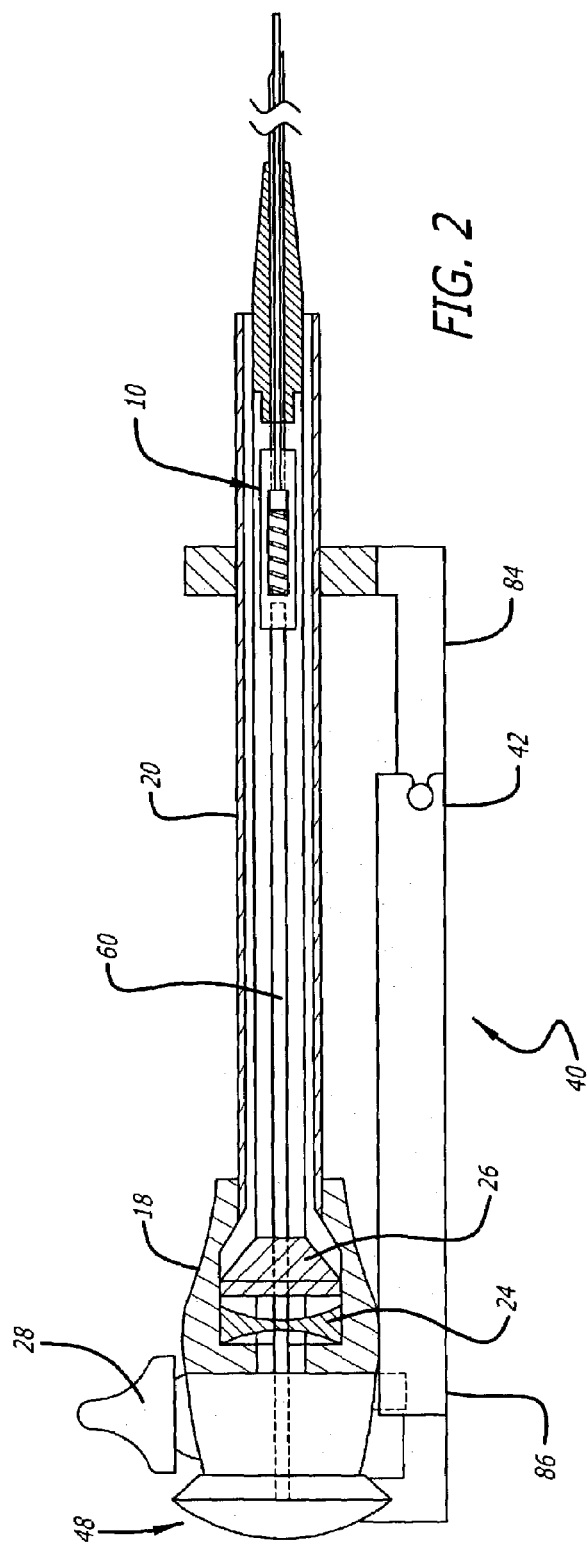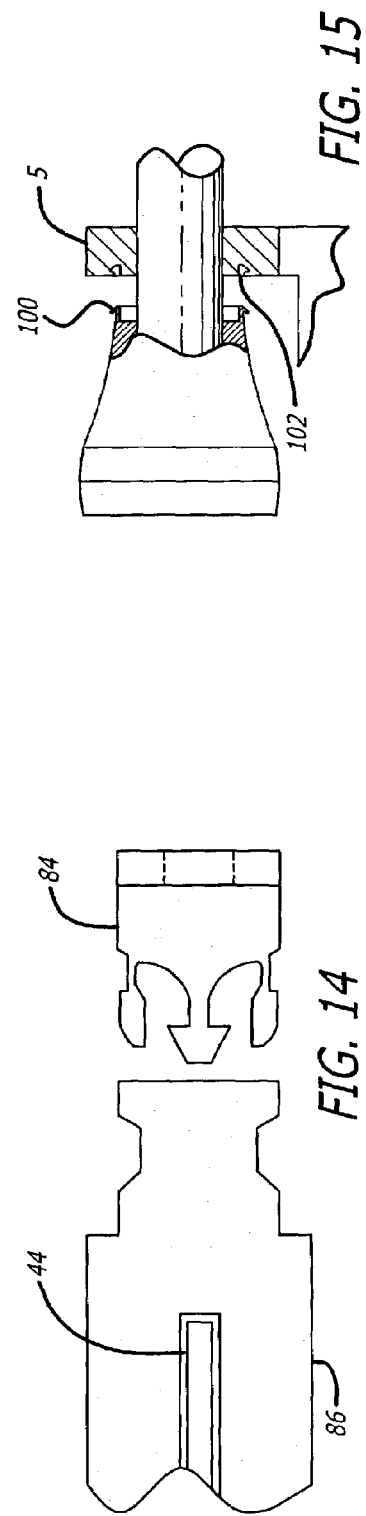

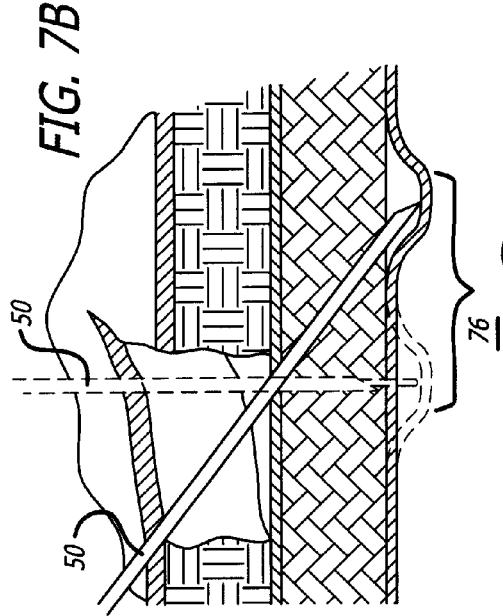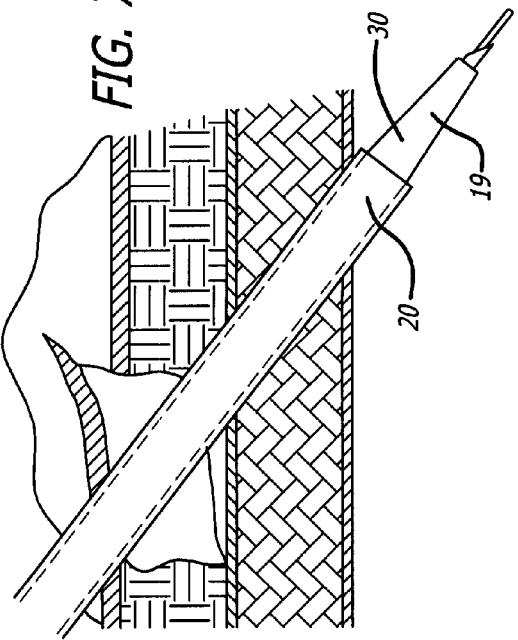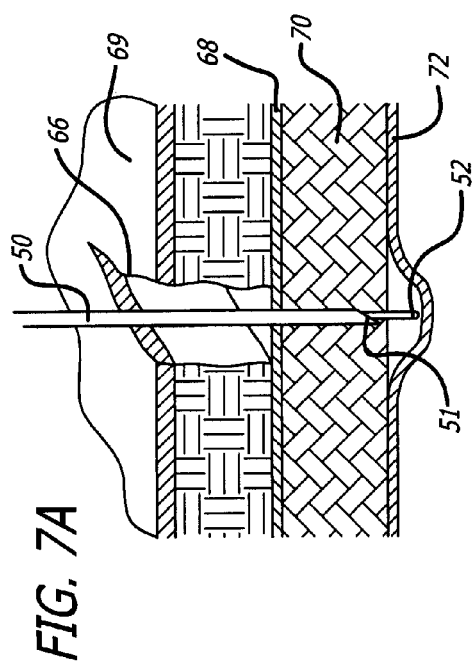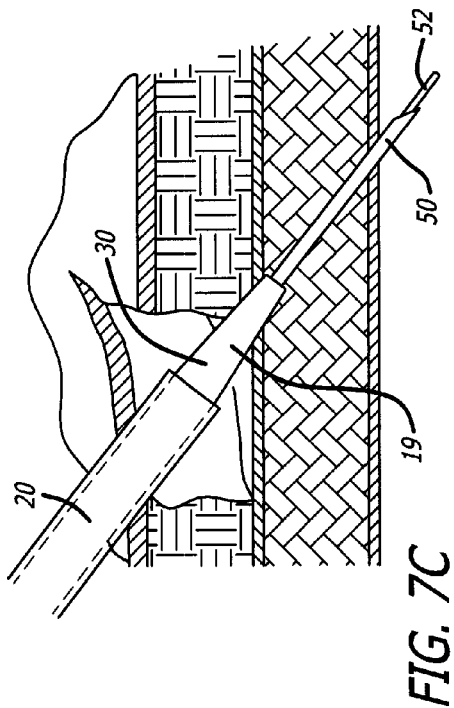

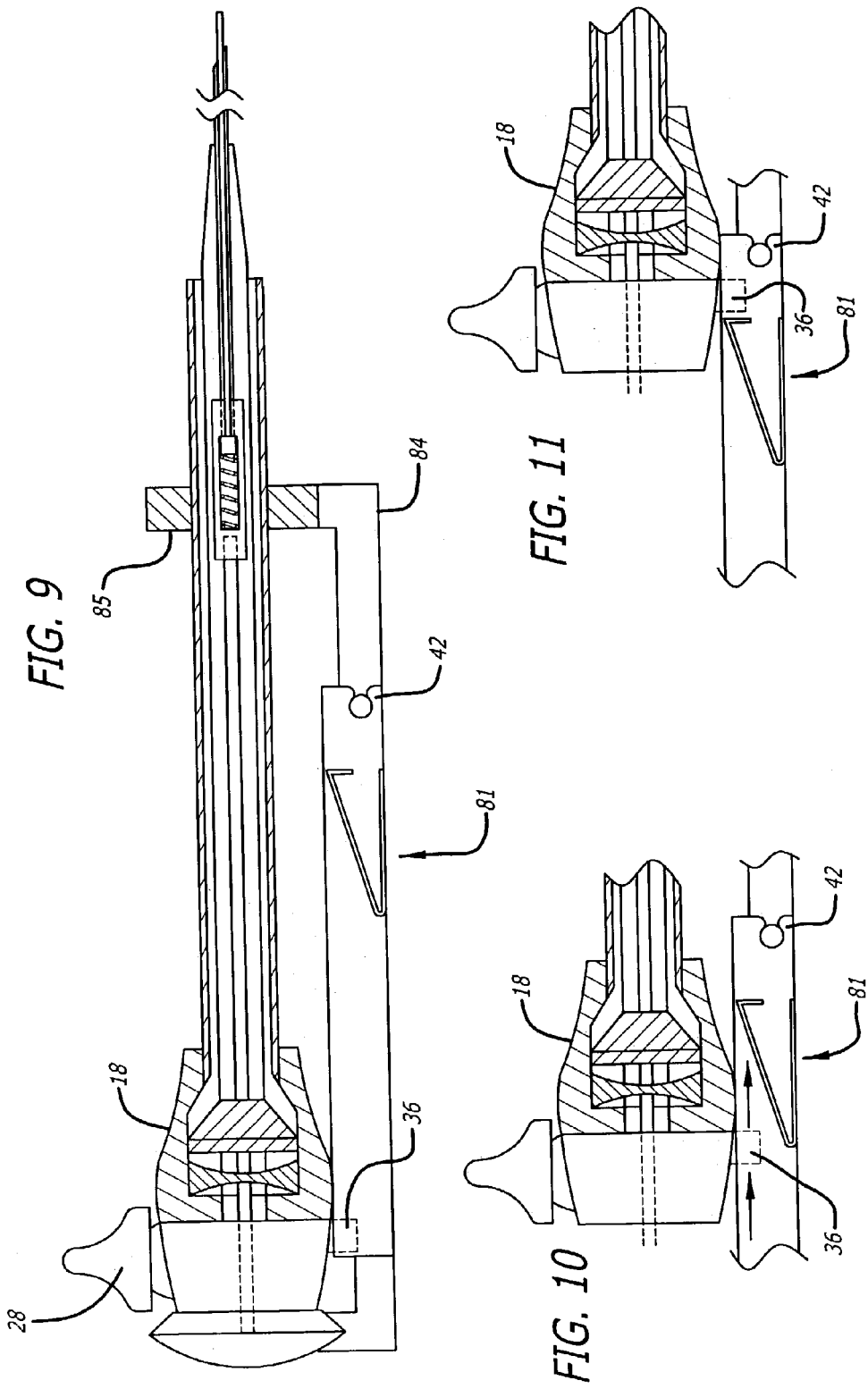

TUNNEL PORT APPARATUS

FIELD OF THE INVENTION

The present invention relates generally to apparatus and methods for surgical placement of a tube apparatus into the body of an organism. More particularly, it relates to apparatus and associated methods for surgical procedures, such as inserting peritoneal dialysis catheters into the peritoneal cavity, for example.

BACKGROUND OF THE INVENTION

Peritoneal dialysis as a modality of renal replacement therapy for end-stage renal disease depends upon functional long-term access to the peritoneal cavity. Access is established by creating a controlled cutaneoperitoneal fistula with a catheter device that bridges the abdominal wall. After infectious complications, mechanical problems are the most common difficulties that threaten the functionality of the catheter. Mechanical problems include flow obstruction from blockage of the catheter tip by omentum, displacement of the intraperitoneal catheter segment to a position of poor drainage function, pericannular leakage of dialysate fluid through the abdominal wall, and hernia formation produced by abdominal wall weakening at the catheter insertion site.

Flow dysfunction produced by catheter obstruction or displacement generally follows 7–31% of catheter implantation procedures. Pericannular leaks and hernias complicate 5–27% of catheter insertions. The consequences of mechanical complications include additional operative procedures to remedy the problem, replacement of the catheter, or loss of the option of peritoneal dialysis as renal replacement therapy with permanent transfer to hemodialysis.

Shifting the catheter insertion site away from the abdominal midline to lateral placement through the body of the rectus muscle has reduced the incidence of pericannular leaks and hernias. Improved results for lateral placement are related to the physical characteristics of the abdominal wall in that lateral location: (i) two thick fascial layers, (ii) the thick body of the rectus muscle, and (iii) propensity for strong tissue ingrowth of anchoring polyester catheter cuffs from the rich muscle blood supply. Although generally improved with lateral placement, the incidence of pericannular leaks continues to range from 0–18%.

Varying degrees of oblique passage of the dialysis catheter through the abdominal wall in a craniocaudad direction have been recommended to maintain pelvic orientation of the catheter thereby reducing the risk of omental entrapment and catheter tip migration. Shorter abdominal wall tunneling was associated with a 9–11% incidence of catheter flow dysfunction while longer tunnels had an incidence rate of 0–3%. My own data revealed a 12.8% incidence of flow obstruction utilizing approximately a 45° oblique passage through the abdominal wall compared to 0.7% incidence associated with a 4–6 cm tunnel through the rectus muscle sheath (Crabtree, unpublished data).

The use of laparoscopically directed percutaneous methods of catheter insertion compared to the more invasive implantation by an open laparotomy incision is generally reported to reduce the incidence of flow dysfunction and pericannular leaks although, exceptions to these findings exist. Using visual guidance, the laparoscopic approach provides more precise intraperitoneal placement of the catheter and less tissue disruption from the standpoint that it constitutes a percutaneous puncture technique (see, for example, "A Laparoscopic Approach Under Local Anesthesia for Peritoneal Dialysis Access", Crabtree, J. H. and Fishman, A., in Peritoneal Dialysis International, vol. 20 pp.757–765, incorporated herein by reference in its entirety).

Despite the general improvements associated with lateral placement, oblique abdominal wall tunneling, and laparoscopically directed percutaneous insertion, the outcomes remain extremely variable. The wide range of reported outcomes stems from a lack of uniformity in implantation tools and methodology. Devices generally used to perform percutaneous insertion and muscular tunneling are borrowed laparoscopic port cannulas that are oversized, possess dangerous trocar blades, and often require considerable modification that departs from the manner of intended use. The variety of available port devices leaves too much variability in application and thus reduces reproducibility and impedes establishing standard methodology for peritoneal dialysis catheter implantation. Abdominal wall tunneling by open dissection is not practical due to the considerable disruption of tissues required to create a passage of sufficient length. The identified problems with existing tools and methods include excessive tissue dissection that may result from open dissection, which increase the risk for pericannular leaks and hernias and limits the length of an abdominal wall tunnel. Additionally, there is an increase in the risk of hemorrhage, leaks, and hernias associated with utilizing trocar-tipped laparoscopic ports with cutting blades and/or oversized laparoscopic ports. Furthermore, laparoscopic ports utilizing an overlying plastic sleeve for radial expansion limit the length of the abdominal wall tunnel. The unsupported plastic sleeve tends to kink in the tissue tract when a guideneedle is removed and prevents safe insertion of a port cannula.

Presently, approximately 12% of the end-stage renal disease population are on peritoneal dialysis. It is projected that this percentage will increase to 20–30% if proper utilization of cannula insertion and placement is practiced.

Clearly, there is a need for a dedicated apparatus specifically designed to provide improved and safe access to internal area/cavities/lumens, etc. of an organism, particularly the peritoneal cavity for implantation of peritoneal dialysis catheters. In particular applications, the apparatus should allow creation of a long oblique tunnel through the muscular abdominal wall without causing significant tissue disruption or risk of hemorrhage. For laparoscopic use, the apparatus should be capable of preserving pneumatic competence of a pneumoperitoneum created by gas insufflation. Desirable physical characteristics of an apparatus for creating access through an abdominal wall, include having minimal dimensions so as to provide passage of a catheter, for example. When utilized for access to the peritoneal cavity, the apparatus should have pneumatic competence for compatibility with laparoscopic techniques. Provided herein is an apparatus and associated methods of use capable of performing intended functions in a simple, accurate, reproducible, and expeditious fashion.

SUMMARY OF THE INVENTION

In particular embodiments, the apparatus of the present invention comprises a guideneedle and a port cannula overlying the guideneedle. The guideneedle can be an assembly that comprises a needle, such as a hollow core guideneedle having a solid core obturator needle therein. The apparatus also includes an obturator rod located within the port cannula (depending upon the pre- or post-operative state of the apparatus) and overlies the guideneedle. Components are held together by a support frame that has an elongated member portion having proximal and distal ends and having support members for supporting said guideneedle and port cannula. The support frame can also have a track along at least a portion of the elongated member portion.

In some embodiments, the guideneedle assembly is joined to the support frame at the proximal end of the support frame. Additionally, the port cannula also further comprises a valve apparatus. The obturator rod, located within the port cannula, can have a cap at its proximal end and may be further comprised of at least one extension member. The at least one extension member is utilized as a guide that follows the track in the support frame along at least a portion of the elongated member portion.

In some embodiments of the apparatus there is an extension member that is a push tab or onto which a push tab may be positioned. In particular embodiments, the support frame also includes at least one disconnect site along its elongated member portion. The apparatus may also have a locking mechanism along its elongated member portion of the support frame.

The teachings of the present invention also provide for a surgical method for obtaining access to an internal space of a subject that comprises preparing a subject for surgery and providing a tunnel port apparatus that is comprised of a support frame having separable proximal and distal portions and a disconnect site. An operator utilizes the support frame as a handle for handling the tunnel port apparatus. An operator includes personnel utilizing the device manually and/or as well as robotically, if the apparatus is so adapted for use with a machine or device that operates automatically or by remote control. An exemplary surgical method entails inserting a guideneedle through an incision and advancing a port cannula and obturator rod over the guideneedle (and/or portions of the guideneedle, such a hollow core guideneedle, for example) and into the desired internal space. Once advanced, and if so provided, a locking mechanism provides for the locking of the port cannula into the advanced position. The operator then disconnects the proximal portion of the support frame from the distal portion of the frame and withdraws the hollow core guideneedle and obturator rod from within the port cannula. This leaves the port cannula, with the distal portion of the support frame, behind and thus provides access to the desired internal space.

The insertion described above is typically performed at a skin incision. Additionally, this method preferably utilizes a laparoscope, introduced through a laparoscopic port that is typically located at a desired and appropriate distance from the insertion site of the guideneedle, such that an operator may monitor the insertion and manipulation of the guideneedle from a perspective within and/or adjacent to the internal space to which access is desired. The teachings of the present invention are particularly applicable when the internal space is a peritoneal space. In such a case, the insertion site of the guideneedle provides for insertion through the anterior rectus muscle and sheath followed by angling of the guideneedle towards the pelvis, forming a tunnel through the sheath.

After introducing and providing the port cannula into peritoneal space, the operator may then introduce a catheter to the internal space via the port cannula. The methods are also applicable to gastrointestinal space and for the introduction of various shunts, for example. The teachings of the present invention are also applicable when the internal space is at least one of a hollow viscus, abscess and lymphocele.

In additional exemplary embodiments, a tunnel port apparatus is herein provided that comprises a support frame including an elongated member portion having a proximal support member and an apertured distal support member extending from the elongated member portion. The elongated member portion includes a track and a guideneedle assembly attached to the proximal support member. A port cannula is provided over said guideneedle assembly and is supported by said apertured distal support member. While the exemplary distal support member described herein provides support through an apertured portion, which may have provided bushings therein for the accommodation of port cannulas/obturator rods of desired diameters, it is further contemplated that support may be provided by a U-shaped support, for example, as well as other supporting configurations. One exemplary configuration comprises a T-bolt configured stud on the distal support member that fits into a track of the port cannula. The track can comprise a slot in the wall of the cannula that extends along at least a portion of the tube and into which the T-bolt fits and provides guidance for the port cannula as it is advanced.

Insertion steps of the port cannula may be considered to have various elements. The physical shape of the resulting tissue tract and the physical force that is utilized by an operator to advance the port cannula through tissue are two of these elements. Conventional port devices establish simple, straight passages through abdominal walls, for example, and in this case the operator is primarily concerned with the force required to advance the port through tissues. This process becomes more complex when it is necessary to simultaneously control both the shape of the tissue tract being formed as well as the force that is used to create the tract. Control of one element is generally maintained at the expense of the other. However, the apparatus of the present invention and its associated method of use provides for the consideration of these as separate steps during cannula port placement, thereby providing greater control, safely and accuracy during the insertion process and formation of a tunnel through tissue. Utilizing the guideneedle assembly in the initial steps permits the operator to concentrate on the position, direction and length of the tissue tract (tunnel). The configuration of the guideneedle assembly provides for improved and relatively facile maneuverability with negligible force due to the small cross section of a hollow core needle (which minimizes force needed to advance through tissue) that is utilized in this initial insertion step. Once positioned through the tissue, the operator can concentrate on applying force required to advance the port cannula over the guideneedle assembly while maintaining the position first provided by the guideneedle.

The foregoing and other objects, features and advantages of the present invention will be apparent to those of skill in the art from the following detailed description which makes reference to several drawing figures which are exemplary and not drawn to actual scale/proportionality.

BRIEF DESCRIPTION OF THE DRAWINGS

FIG. 2 is a cross-sectional side view along line 2—2 of the apparatus of FIG. 1;

FIGS. 7A–G depict exemplary method steps utilizing an exemplary tunnel port apparatus, according to the teachings of the present invention;

FIG. 9 is a schematic cross-section depicting an exemplary locking device;

FIG. 10 is a side cross-sectional view of a portion of the apparatus in a pre-advanced position;

FIG. 11 is a side cross-sectional view of a portion of the apparatus having the port cannula and obturator rod in the advanced, locked position;

FIG. 14 is a top view of an exemplary locking and release mechanism at a disconnect site, in accordance with the teachings of the present invention;

FIG. 15 is a side view of an exemplary mechanism for locking the rim of the valve apparatus to the face of an apertured portion.

DETAILED DESCRIPTION OF THE INVENTION

Figure 1:
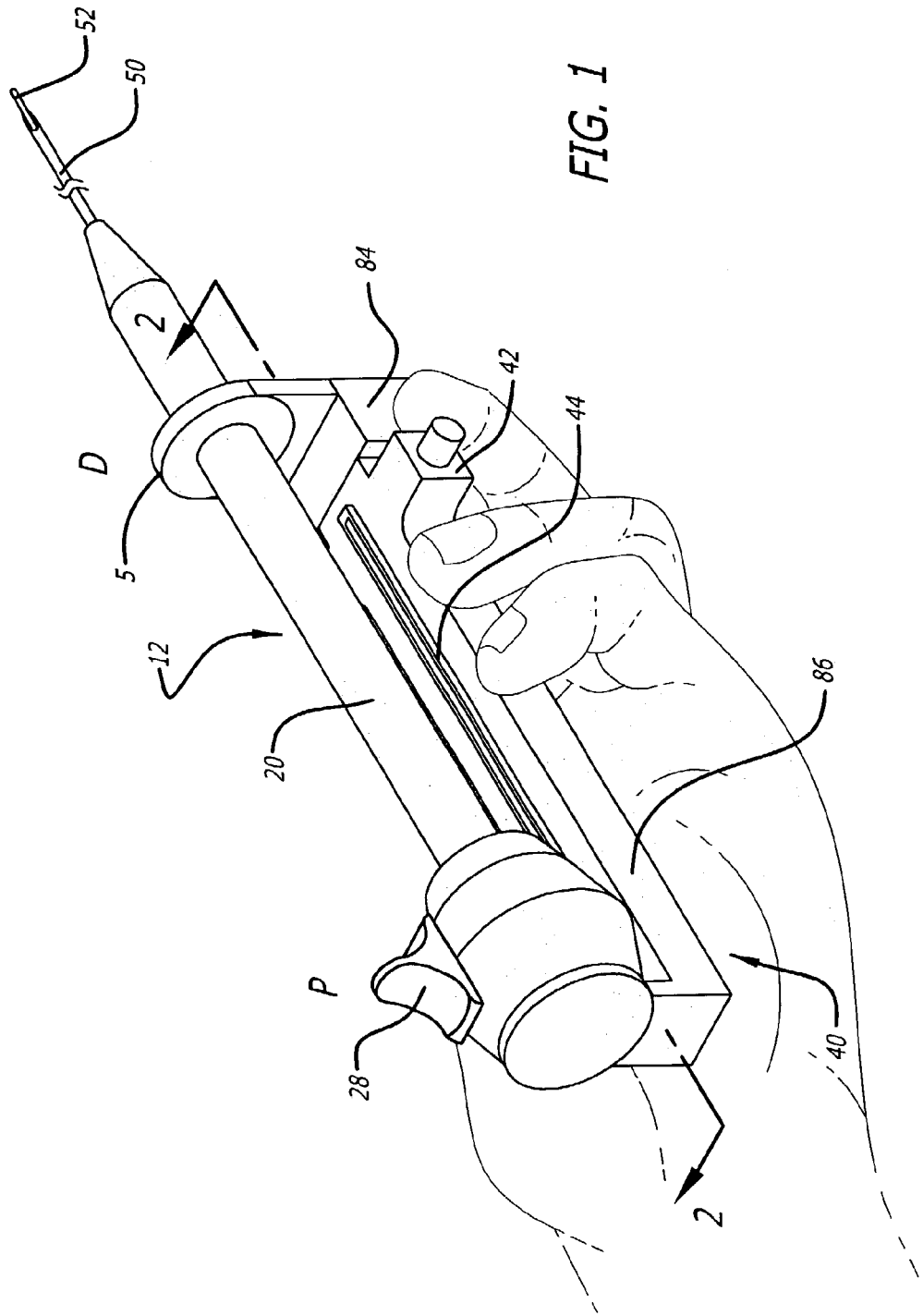
FIG. 1 is an exemplary figure of a tunnel port apparatus according to the teachings of the present invention, in a procedure-ready state.

Now turning to FIG. 1, an exemplary tunnel port apparatus is depicted being held by an operator in an exemplary grip. Components of the apparatus comprise a guideneedle assembly 10 (not shown, see FIGS. 2 and 6) with overlying port cannula 12 in conjunction with a support frame 40. Support frame in this embodiment has a proximal frame portion 86 and a distal frame portion 84, which has an apertured portion 5 that supports the hollow tube 20 of port cannula 12. The guideneedle assembly 10 and port cannula 12 are designated to have a proximal end (P) that is oriented toward the operator of the apparatus and a distal end (D) that is oriented toward a subject, such as an animal, including humans.

Figure 3:
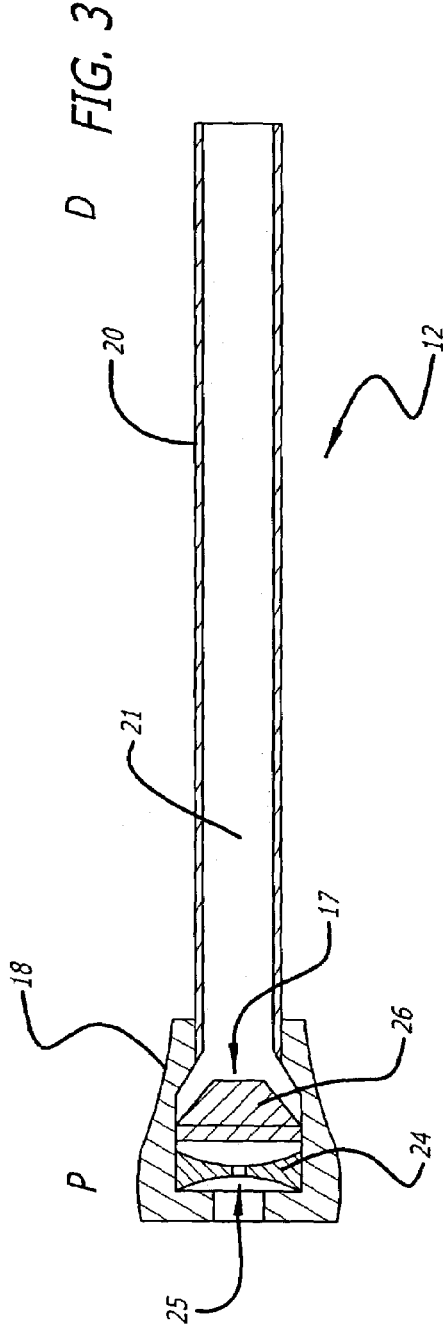
FIG. 3 is another cross-sectional side view along line 2—2 of components of FIG. 1 and depicts exemplary component parts of a port cannula consisting of a pneumatically competent valve apparatus and hollow port tube.

The port cannula 12 comprises a proximal valve apparatus 18 and a distal hollow tube 20 (FIGS. 2 and 3). The valve apparatus 18 comprises a channel passage 17 inline with the axis of the lumen 21 of the distal hollow tube 20. The valve apparatus 18 comprises a perforated elastic membrane 24 (apertured diaphragm, for example) placed proximal in sequence to a valve 26, such as an elastic non-return flap valve, such as an exemplary duckbill valve or other valves, as known in the surgical/medical device arts. The valve mechanism (apertured diaphragm in sequence with a duckbill non-return flap valve) in the port cannula 12 is found in most commercially available laparoscopic port devices and other cannula systems used in medicine that require a seal assembly. Perforation 25 in the perforated elastic membrane 24 is the smallest aperture possible that permits passage of desired items, such as obturator rod 30 and dialysis catheter 78 (and associated components, such as cuffs) or any other appropriately sized catheters (such as, but not limited to, shunts, drains and infusion tubes). The elastic properties of elastic membrane 24 are such that it maintains a snug airtight seal around the components of the obturator rod 30 and dialysis catheter 78 as they traverse the perforated elastic membrane 24. Valve 26, here depicted as a duckbill flap valve, contains sufficient elastic properties to allow it to resume its shape after deformation from the passage of the port cannula obturator 30 and dialysis catheter 78. The bivalve leaflets of the duckbill flap valve coapt to form an airtight seal when the pressure distal to the valve exceeds that proximal to it. The distal hollow tube 20 of the port cannula 12 is the smallest diameter that allows passage of the components of the peritoneal dialysis catheter 78. The hollow tube 20 is provided with sufficient length, for example, so as to traverse an abdominal wall through a long oblique tunnel to reach a peritoneal cavity.

Figure 4:
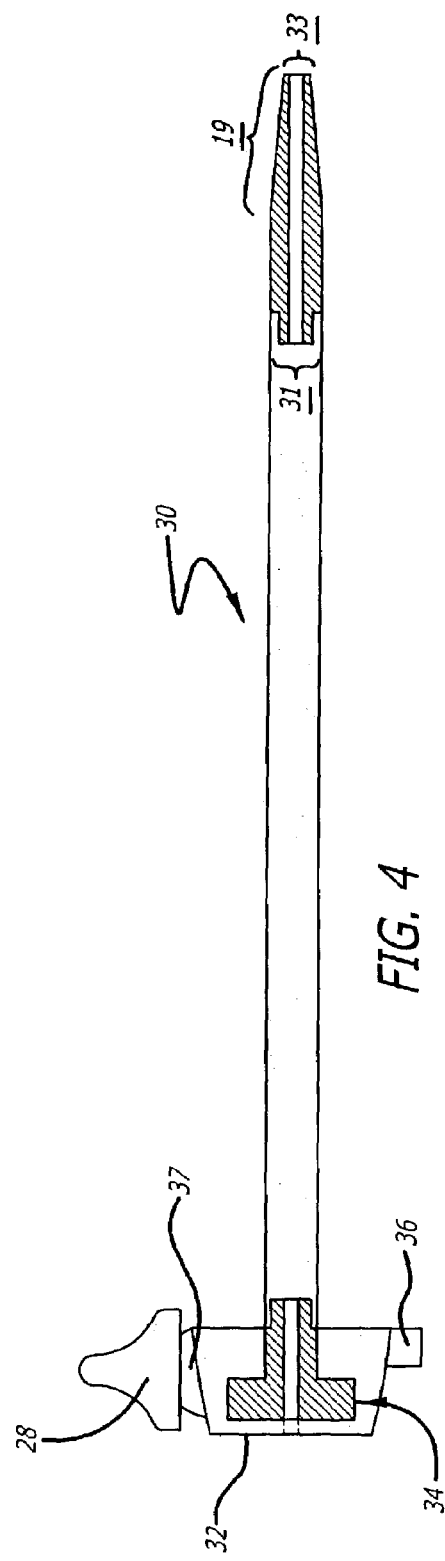
FIG. 4 is still another cross-sectional side view along line 2—2 depicting exemplary component parts of cannula obturator rod.

Port cannula 12 contains an obturator rod 30 that passes through its hollow long axis (FIGS. 2 and 4). The obturator rod 30 extends beyond the length of the port cannula 12 at its proximal end to comprise a cap 32 over the proximal end of the port cannula 12. Also and within cap 32, is an obturator cap flange 34, which serves to stabilize and center steel tube/rod 60. Extension bars 36 and 37 arise from cap 32 and are substantially perpendicular to the long axis of the obturator rod 30. Attached to extension bar 37 is a push-tab 28 suitable for grasping by an operator for advancing the obturator rod 30 along the length of at least a portion of guideneedle assembly 10. In this embodiment, extension bar 36 serves as a rudder device that extends into at least one track 44, which may be recessed, of a support frame 40 and serves to stabilize the apparatus by directing forces exerted on push-tab 28 to the long axis of the apparatus.

Obturator rod 30 extends beyond the length of port cannula 12 at its distal end (FIGS. 1 and 2). The segment of obturator rod 19 that extends beyond the length of port cannula 12 is conically tapered (FIG. 4). The proximal diameter 31 of the taper at the distal end of port cannula obturator 30 approximates the internal diameter of port cannula 12. The diameter of the taper at its distal end 33 approximates the outside diameter of a component of guideneedle assembly 10, such as hollow core guideneedle 50. The angle of the taper provides sufficient length of its conical shape to create a gradual transition from the outside diameter of the hollow core guideneedle 50 to approximately the outside diameter of the port cannula 12. A tapered obturator rod 30, when advanced through tissue, creates a tissue tract by radial expansion. In contrast, standard trocar devices use cutting blades to penetrate tissue, such as an abdominal wall, for example. The defects caused by the radially expanding devices are about 50% smaller and the risk of hemorrhage is negligible compared to standard trocar blades.

Figure 5:
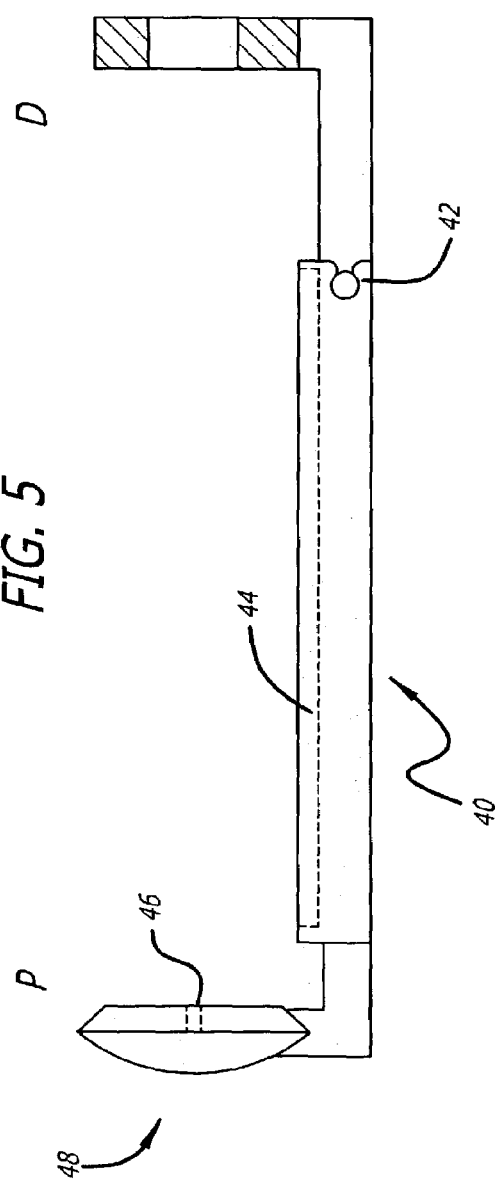
FIG. 5 is another cross-sectional side view along line 2—2 illustrating general features of an exemplary support frame according to the teachings of the present invention.
Figure 6:
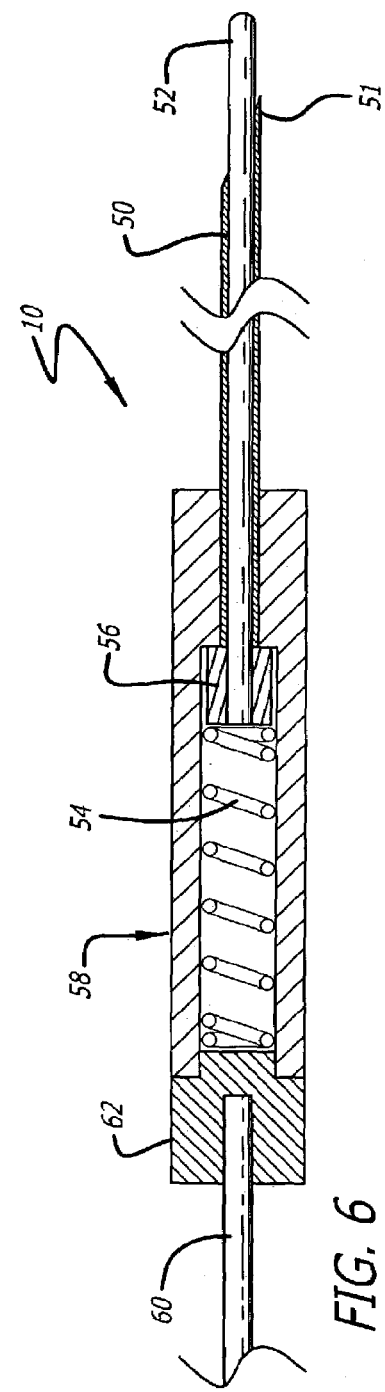
FIG. 6 is a schematic partial cross-sectional view illustrating a spring mechanism portion of a suitable exemplary guideneedle assembly.

The guideneedle assembly 10 may be permanently attached to the support frame 40 at its proximal end via steel tube/rod 60 that fits within a support 46 located at a rear portion 48 of the support frame (FIGS. 5 and 6). Steel tube/rod 60 is in communication with a chamber plug 62 at its opposite end. The total length of the guideneedle assembly 10 is the sum of the overlying length of the port cannula 12 with associated obturator rod 30 and a distal exposed length sufficient to traverse the abdominal wall through a long oblique tunnel to reach the peritoneal cavity. The distal end of a hollow core guideneedle 50 is provided with a sharp bevel tip 51, similar to a hypodermic needle, and is capable of penetrating tissues. Within the hollow core guideneedle 50 is a spring loaded solid core obturator needle 52 with a blunt rounded tip that extends beyond sharp bevel tip 51 and is sufficient to prevent its sharp tip from being exposed in a resting, unstressed state. Pressure on the tip of the solid core obturator needle 52 causes it to recede into the hollow core guideneedle 50 and against a spring coil 54, via rod cap 56 in spring coil chamber 58, that in turn is compressed into a stressed state. Recession of the solid core obturator needle 52 causes the sharp bevel tip 51 of the hollow core guideneedle 50 to become exposed. Release of pressure on the solid core obturator needle 52 tip allows the stress-loaded spring to protract the solid core obturator needle 52 to its former unstressed location thereby covering up the sharp bevel tip 51 of the hollow core guideneedle 50.

The guideneedle assembly 10 and port cannula 12 with associated obturator rod 30 are provided with a support frame 40 that serves to hold the various parts together as one working piece and provides a handle for the operator to hold while using the device (FIGS. 1 and 5). In a particular embodiment, support frame 40 is provided with a disconnect site 42 that allows support frame 40 to be disassembled into at least two pieces so that particular elements (such as the guideneedle assembly 10, obturator rod 30, and attached proximal frame portion 86) of the apparatus can be removed as a single unit from the field of operation and discarded after port cannula 12 has been inserted into the subject. The port cannula 12 with attached distal frame portion 84 provides access to the peritoneal cavity during catheter implantation In one embodiment, the support frame 40, in addition to its function of holding the various parts together as one working piece, has at least one disconnect site 42 provided with locking and releasing mechanisms, as exemplary depicted in the figures provided herein, to assure safe utilization of the present invention. These mechanisms include, but are not limited to, slot and hinge configurations, snaps, magnets, magnetic buttons, fasteners, buckles and side-release buckles as well as other configurations.

As known in the surgical arts, support frame 40, and components thereof, may be comprised of and manufactured by a number of well known materials and techniques, such as plastics, polymers, alloys, resins, metals etc . . . that are amenable to appropriate manufacturing techniques such as casting, molding, injection molding, forging and other manufacturing process and techniques well known in the medical device arts. Furthermore, at least some portions of the apparatus of the present invention may require sterilization. As such, in accordance with the teachings of the present invention, materials used should be able to withstand standard sterilization techniques without damage, distortion, or loss of material integrity or function.

Figure 12:
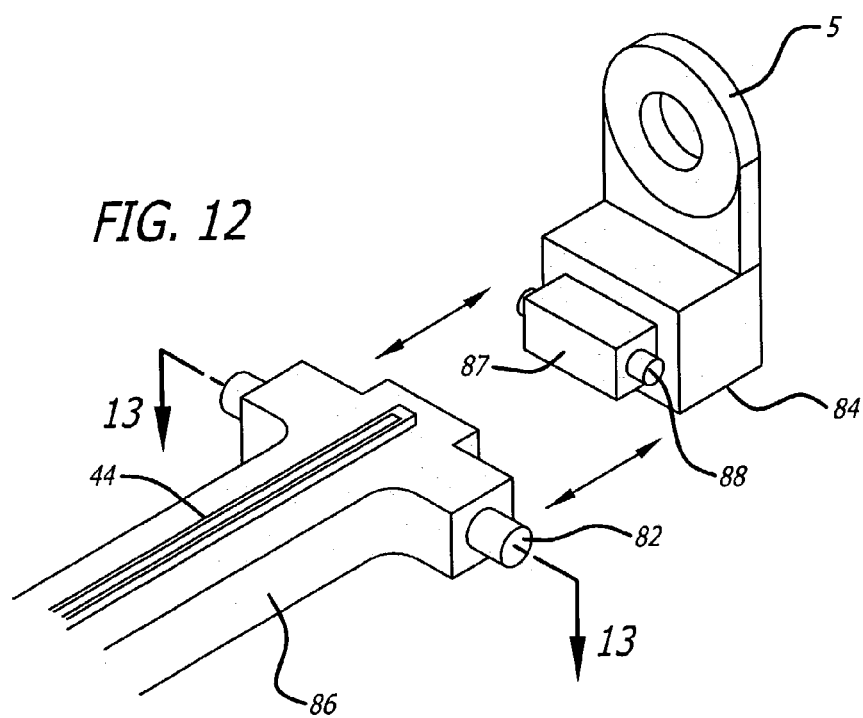
FIG. 12 is a perspective view of an exemplary disconnected support frame.
Figure 13:
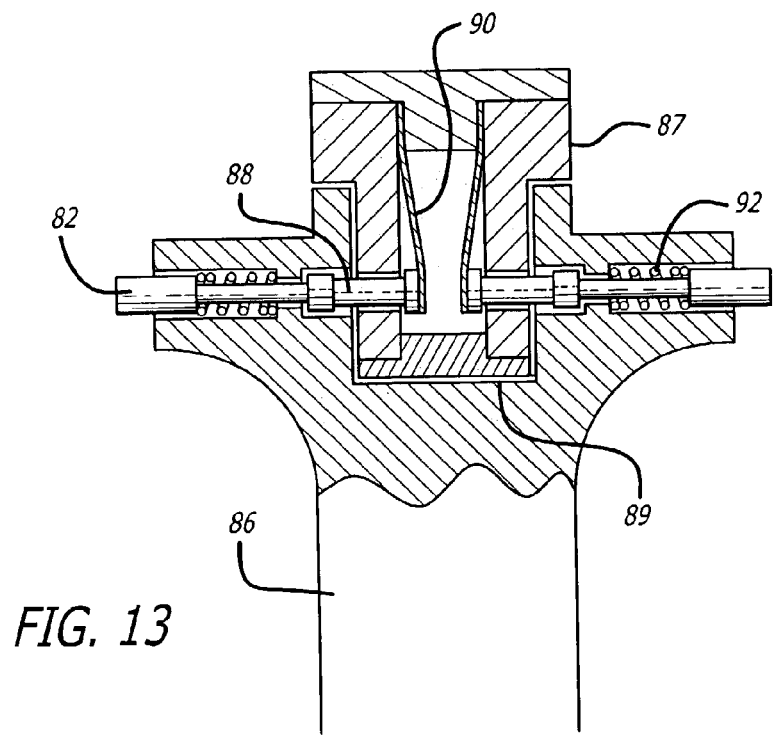
FIG. 13 is a cross-sectional view of FIG. 12 along line 13—13 depicting exemplary locking mechanisms for locking/separating portions of support frame.

There are many connecting configurations that may be utilized at disconnect site 42 of support frame 40 that render the two support frame portions, proximal frame portion 86 and distal frame portion 84, in releasable communication with each other. For, example a simple friction fit may be utilized to hold support frame 40 together. Other more robust, exemplary frame disconnect mechanisms (lock and release mechanisms), such as the exemplary spring and locking-pin configuration depicted in FIGS. 12 and 13, are also contemplated. In this example, proximal frame portion 86 is provided with springs 92 in communication with release buttons 82 and is configured such that a recessed portion 89 of proximal frame portion 86 provides a complementary fit with an extended portion 87 of distal frame portion 84 having locking pins 88 in communication with leaf-type springs 90, for example. Turning to FIG. 13, once distal frame portion 84 is fitted into proximal frame portion 86, the two frame portions are in releasable communication. In order to separate the frame portions, release buttons 82 are depressed, thus depressing locking pins 88 medially and allowing frame portions 86 and 84 to be separated.

Another exemplary mechanism is depicted in FIG. 14. Here, proximal frame portion 86 and distal frame portion 84 may have complementary portions of a buckle in order to fasten portions of support frame 40 in releasable communication with each other. The depicted embodiment in FIG. 14 utilizes a side-buckle type configuration. Of course, the separate components of the locking and/or release mechanism may be on either one or the other pieces (distal/proximal) of the apparatus that are to be releasably joined.

The apparatus may be configured for single-use not only for an individual subject, but also for each insertion in that subject. After the port cannula 12/obturator rod 30 has been advanced, the obturator rod 30 is locked into position in the support frame 40 so that it cannot be withdrawn and advanced again, as exemplified in FIGS. 9–11 and discussed below. The intent is to prevent the operator of the device from repeatedly withdrawing and readvancing the port cannula 12/obturator rod 30 through the rectus muscle, for example, thereby increasing the risk of hemorrhage or creating a patulous tissue tract. Exemplary locking mechanisms are provided below. In addition, the obturator rod 30 is locked in a position that supports and covers a significant portion of the hollow core guideneedle 50 and minimizes the risk that the disassembled device will produce injury to the subject, operator, or ancillary personnel.

Frame disconnect mechanism(s) at disconnect site 42 provides support frame 40 the ability to be disassembled so that the nonessential used element can be removed as one piece from the field of operation. The release mechanism is designed to minimize the risk of accidental disengagement. In particular embodiments, two release buttons are provided that require simultaneous compression before the support frame 40 can be separated, at shown in exemplary FIG. 12.

Turning to FIGS. 9–11, an exemplary locking mechanism 81, such as a spring-type lock over which extension tab 36 may slide over, may be provided and be mounted on support frame 40, that that locks obturator rod 30 in the forward position when fully advanced. There are many locking configurations that may be utilized to secure the obturator rod 30 in the forward position. These include, but are not limited to, friction fits, snaps, catches or fasteners.

Valve apparatus 18 may be secured to the distal frame portion 84 of support frame 40 by a locking configuration when obturator rod 30 has been fully advanced. There are many locking configurations that may be utilized to secure the valve apparatus 18 in the forward position. These include, but are not limited to, friction fits, snaps, catches or fasteners. For example, as exemplarily depicted in FIG. 15, a recessed groove 100 in the face of apertured portion 5 is provided and configured to accept the rim of the valve apparatus 18, which may be provided with interlocking snaps 102 so that valve apparatus 18 cannot be separated once the valve apparatus 18 has been seated in the forward position and locked.

Figure 7E:
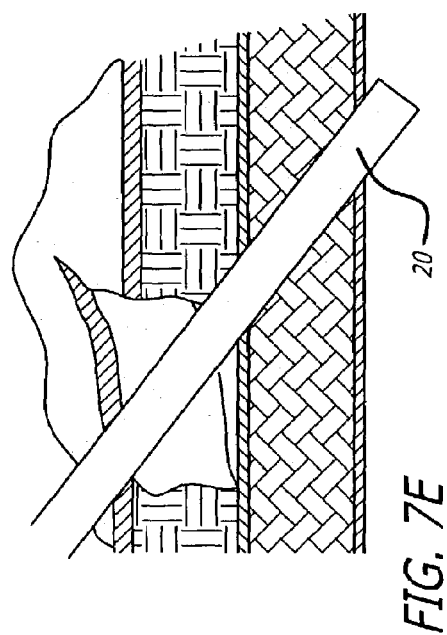

Turning to FIGS. 7A–G, an exemplary method of use for the disclosed apparatus is depicted. Firstly, a pneumoperitoneum is created and a laparoscope (not shown) is inserted at an abdominal wall location remote from the designated peritoneal dialysis catheter insertion site, using standard laparoscopic surgical methods (see "A Laparoscopic Approach Under Local Anesthesia for Peritoneal Dialysis Access", Crabtree, J. H. and Fishman, A., in Peritoneal Dialysis International, vol. 20 pp. 757–765, for example). At the designated catheter insertion site, the fascia of the rectus abdominus muscle is exposed through an incision 66 in the skin 69 and subcutaneous tissues. The apparatus in its procedure-ready state is shown in FIG. 1. The hollow core guideneedle 50 of the apparatus is inserted perpendicular to the abdominal wall through the anterior layer of the muscle fascia 68 (FIG. 7A). The density of the fascia offers sufficient resistance that the sharp beveled tip 51 of the hollow core guideneedle 50 becomes exposed and permits penetration. The underlying muscle tissues 70 offer minimal resistance and the solid core obturator needle 52 springs back to cover the sharp beveled tip 51. The hollow core guideneedle 50 is advanced through the rectus muscle in perpendicular fashion. The blunt tip of the solid core obturator needle 52 is easily seen through the laparoscope as it tents down the posterior fascia 72 of the rectus muscle. The hollow core guideneedle 50 is then angled toward the pelvis and advanced with the blunt tip of the solid core obturator needle 52 observed laparoscopically as it is easily slid down the posterior fascia 72 of the rectus muscle (FIG. 7B). When the desired tunnel length 76 within the rectus fascial sheath has been obtained, from about 4 to 12 cm, preferably from about 7 to 10 cm, the hollow core guideneedle 50 is angled toward the peritoneal cavity. Pressure on the posterior fascia 72 and peritoneum causes the sharp beveled tip 51 of the hollow core guideneedle 50 to become exposed and permits entry into the peritoneal space. The hollow core guideneedle 50 has established a long oblique tunnel through the muscular abdominal wall.

The long oblique tunnel through the rectus sheath created in a craniocaudad direction promotes pelvic orientation of the catheter 78. Compared to a catheter 78 that passes perpendicularly through the abdominal wall, the potential range of motion of the catheter 78 is reduced by nearly half. Rectus sheath tunneling in conjunction with other auxiliary procedures, such as deep pelvic placement and omentopexy for redundant omentum, has all but eliminated occurrences of catheter flow dysfunction.

Figure 8:
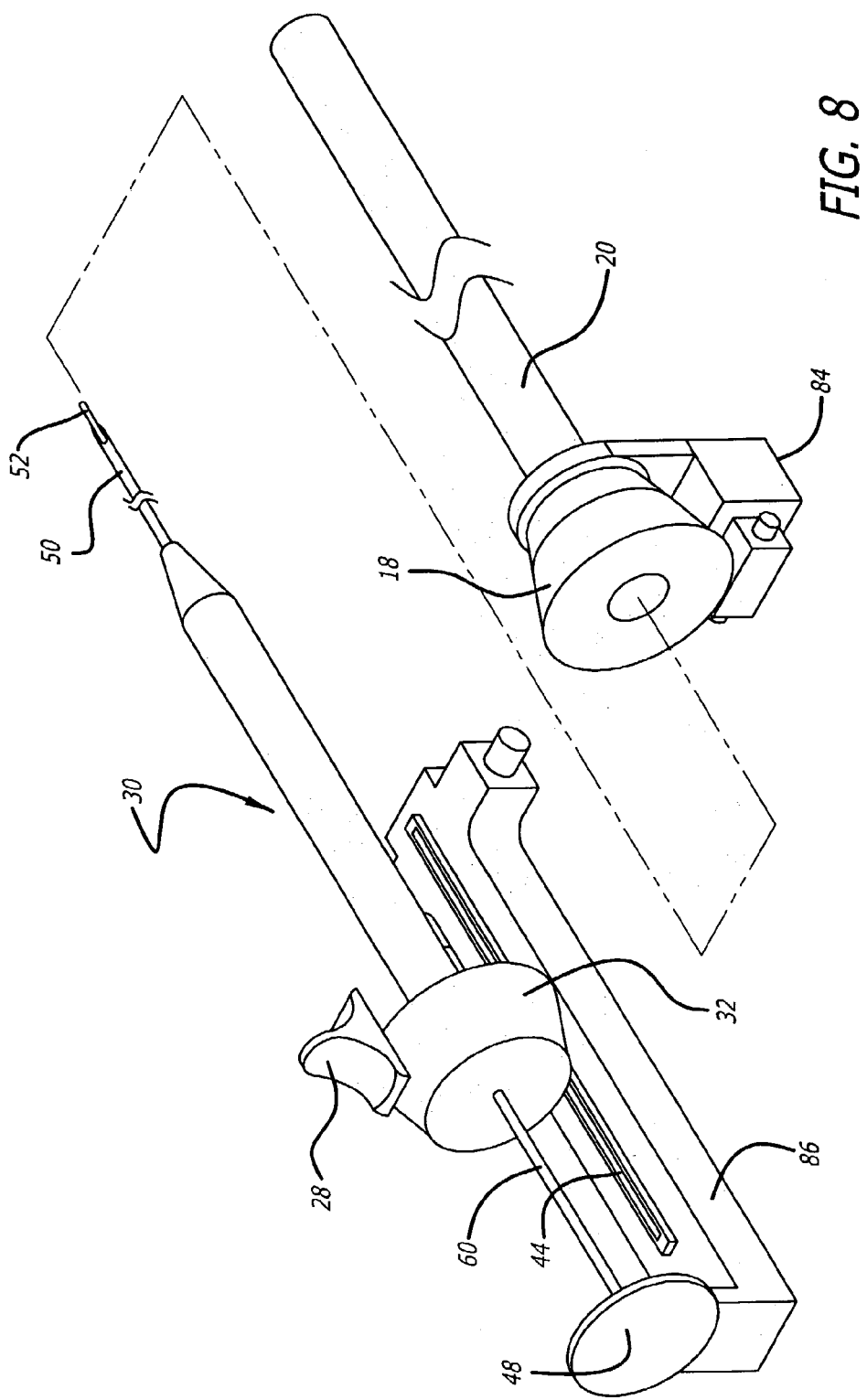
FIG. 8 is a drawing depicting an exemplary tunnel port apparatus in a separated post-procedural state.

Steadying the frame with one hand while using push-tab 28 on the cannula obturator rod 30 with the other, the distal hollow tube 20 of the port cannula 12 is advanced over the hollow core guideneedle 50 through the abdominal wall into the peritoneal space (FIG. 7C, D). This maneuver is monitored with the laparoscope to assure that the device is not inadvertently shifted in position and to confirm proper insertion of the port cannula 12 and its hollow tube 20. Support frame 40 is separated at the disconnect site 42 permitting withdrawal and discard of the guideneedle assembly 10, obturator rod 30, and the proximal frame portion 86 of the support frame 40 as a single unit (FIG. 8). This completes the port cannula 12 insertion process (FIG. 7E).

Figure 7F:
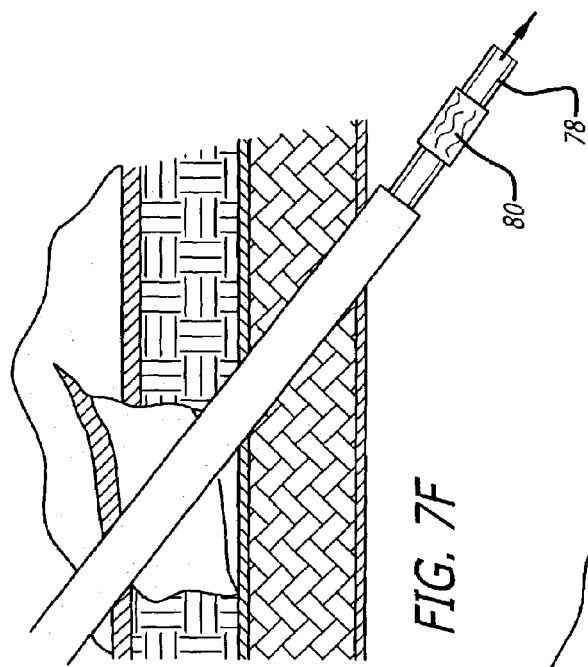
Figure 7G:
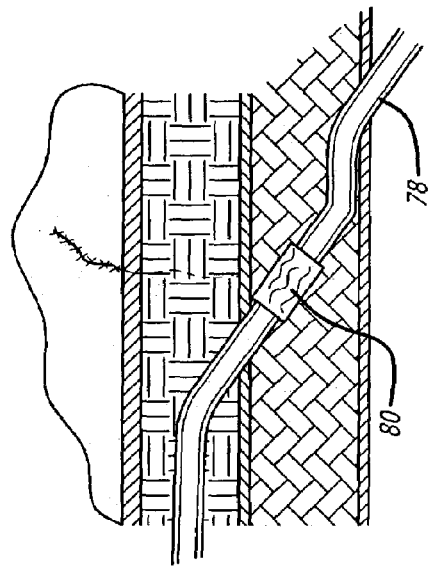

The peritoneal dialysis catheter 78 having cuffs, as shown at 80, straightened with a stylet provided by the manufacturer (not shown), is advanced through the port cannula's 12 hollow tube 20 under laparoscopic control (FIG. 7F). After satisfactory placement of the dialysis catheter 78, the port cannula 12 (and hollow tube 20) and stylet are withdrawn. Exiting the catheter through a small skin incision, removing the laparoscopic instruments, and closing the wounds using standard surgical techniques for implanting peritoneal dialysis catheters (see,"A Laparoscopic Approach Under Local Anesthesia for Peritoneal Dialysis Access", Crabtree, J. H. and Fishman, A., in Peritoneal Dialysis International, vol. 20 pp.757–765) completes the procedure (FIG. 7G).

The small defect created by radial expansion and a long oblique passage through the abdominal wall reduces the incidence of leaks and hernias. In the event that it is desirable for catheter 80 to be subsequently removed, the risk of hernia should be low because there is considerable offset of holes made in the anterior and posterior rectus sheath, as known in the peritoneal dialysis art.

A beneficial feature of the described apparatus is that it is one piece in the procedure-ready state and two pieces in the post procedure state. In the operating room environment, where all needles and instruments must be accounted for, an apparatus with a limited number of separate pieces is a positive attribute.

It is also contemplated that the present apparatus may be provided as part of a catheter insertion surgical kit that may be comprised of, in addition to the apparatus of the present invention, appropriate catheter or catheters and/ or stylet(s) and associated surgical instruments/components. The kit, or components thereof, may all be provided as a single sterile package (for example tunnel port apparatus, stylet, catheter), or individual instruments/components/apparatus of the kit may each be packaged and provided individually in sealed sterile packages as part of a larger kit.

While the present disclosure has been focused on peritoneal insertion methods and applications, the present invention is by no means so limited. Other applications in which placement of a tube device into the peritoneal cavity that can be facilitated with the apparatus of the present invention include, but are not limited to, catheters for ventriculoperitoneal or ventriculopleural shunts and peritoneovenous shunts. Tubes can be inserted into various portions of the gastrointestinal tract for purposes of infusion or drainage.

Ventriculoperitoneal and ventriculopleural shunts are utilized to treat hydrocephalus. Abnormalities resulting in obstruction of cerebrospinal fluid circulation can lead to dilatation of the cerebral ventricular system and increased intracranial pressure. Treatment consists of inserting a silastic tube in the lateral ventricle and routing it subcutaneously to either the pleural space or peritoneal cavity. Insertion of the tube into either the pleural space or peritoneal cavity can be accomplished according to the teachings of the present invention.

Patients with refractory ascites (fluid accumulation in the peritoneal cavity due to malignant disease or liver disease) are sometimes managed by decompressing the fluid with a tube that shunts the peritoneal fluid to the venous system. The placement of the abdominal tube can be facilitated utilizing the teachings of the present invention.

Laparoscopic directed cannulation of the stomach or small intestine for purposes of inserting a feeding tube or decompressing tube can be facilitated with the present invention. Although requiring modifications in size to accommodate the specific application, the principles regarding method of use would be the same. The apparatus could also be used to laparoscopically assist in placing a drain into a hollow viscus, e.g., gallbladder or bladder, or tube decompression of a fluid collection such as an abscess or lymphocele, for example.

The invention has now been explained with reference to specific embodiments. Other embodiments will be apparent to those of ordinary skill in the art in view of the foregoing description. It is not intended that this invention be limited except as indicated by the appended claims and their full scope equivalents.

We claim:

1. A tunnel port apparatus comprising:
   a guideneedle assembly having a guarded hollow core guideneedle, the hollow core guideneedle including a solid core obturator needle;
   a blunt-tip port cannula overlying said guideneedle assembly;

a tapered blunt obturator rod within said port cannula and overlying said guideneedle assembly; and a support frame including an elongated member portion having proximal and distal ends and from which support members extend in the same direction therefrom supporting said guideneedle assembly and port cannula;

wherein the guideneedle assembly extends outward at an original position relative to the port cannula and obturator rod to create a tunnel for insertion of the port cannula, the port cannula and obturator rod extending to a position overlying the guideneedle assembly during insertion of the port cannula.

2. The apparatus of claim 1 wherein said guideneedle assembly is joined to said support frame at said proximal end of said support frame.

3. The apparatus of claim 1 wherein said port cannula further comprises a valve apparatus.

4. The apparatus of claim 1 wherein said support frame includes a track along at least a portion of said elongated member portion.

5. The apparatus of claim 1 wherein said obturator rod has a cap at its proximal end.

6. The apparatus of claim 5 wherein said cap further comprises at least one extension member.

7. The apparatus of claim 6 wherein said at least one extension member is a guide that follows a track in said support frame.

8. The apparatus of claim 6 wherein said at least of extension member is a push tab.

9. The apparatus of claim 1 wherein said support frame includes at least one disconnect site along said elongated member portion.

10. The apparatus of claim 1 further comprising a disconnect site.

11. The apparatus of claim 1 further comprising a locking mechanism along said elongated member portion of said support frame.

12. A tunnel port apparatus comprising:

a support frame including an elongated member portion having a proximal support member and an apertured distal support member extending substantially perpendicular from said elongated member portion, said elongated member portion including a track;

a guideneedle assembly having a guarded hollow core guideneedle, the hollow core guideneedle including a solid core obturator needle attached to said proximal support member; and a blunt-tip port cannula over said guideneedle assembly and supported by said apertured distal support member wherein the guideneedle assembly extends outward at an original position relative to the port cannula and obturator rod to create a tunnel for insertion of the port cannula, the port cannula and obturator rod extending to a position overlying the guideneedle assembly during insertion of the port cannula.

13. A tunnel port apparatus comprising:

a support frame including an elongated member portion having proximal and distal ends from which support members extend substantially perpendicular therefrom;

a disconnect site between said proximal and distal ends;

a guideneedle assembly including a guarded hollow core guideneedle, the hollow core guideneedle including a solid core obturator needle;

a blunt-tip port cannula overlying said guideneedle assembly; and a tapered blunt obturator rod within said port cannula and overlying said guideneedle assembly, wherein said guideneedle assembly has a cross-sectional profile which minimizes force application during formation of a tissue tract wherein the guideneedle assembly extends outward at an original position relative to the port cannula and obturator rod to create a tunnel for insertion of the port cannula, the port cannula and obturator rod extending to a position overlying the guideneedle assembly during insertion of the port cannula.

* * * * *